United States Patent [19]

Stoller et al.

[11] Patent Number: 4,557,271
[45] Date of Patent: Dec. 10, 1985

[54] METHOD AND APPARATUS FOR DETECTING BODY ILLNESS, DYSFUNCTION, DISEASE AND/OR PATHOLOGY

[76] Inventors: Kenneth P. Stoller, 341 S. Bentley Ave., Los Angeles, Calif. 90049; Barry E. Taff, 8665 Pickford St., Los Angeles, Calif. 90035

[21] Appl. No.: 493,707

[22] Filed: May 11, 1983

[51] Int. Cl.$^4$ ............................................. A61B 5/05
[52] U.S. Cl. .................................... 128/734; 128/639
[58] Field of Search ....................... 128/734, 783–786, 128/795, 796, 798, 419 P, 419 R, 639, 644, 640–643, 800–802, 803, 799, 774, 779

[56] References Cited

U.S. PATENT DOCUMENTS

| 3,971,366 | 7/1976 | Motoyama | 128/734 |
| 4,004,578 | 1/1977 | Palmius | 128/640 |
| 4,325,367 | 4/1982 | Topper | 128/795 |

FOREIGN PATENT DOCUMENTS

| 2552035 | 5/1977 | Fed. Rep. of Germany | 128/642 |

OTHER PUBLICATIONS

Leask et al, "A Multi-Pole Printed Circuit Electrode", Lancet, 5-16-64.

*Primary Examiner*—Lee S. Cohen
*Assistant Examiner*—Steven Falk
*Attorney, Agent, or Firm*—Philip D. Junkins

[57] ABSTRACT

A method and apparatus for non-invasively measuring and analyzing bilateral D.C. bioelectric potentials associated with organized electrical field patterns about discrete anatomical sites on the dermal surface (skin) of human subjects for the purpose of generating data for use by medical practitioners in diagnosing existing or impending illness, dysfunction, disease and/or pathology. The apparatus simultaneously measures D.C. potentials at 10 to 14 bilateral dermal sites through multipoint voltage sensing electrodes and develops a maximum bilateral D.C. potential differential value for each sensed point at each sensing site with respect to a ground potential. The apparatus compares the highest differential voltage values of the right body sites with the highest differential voltage values of the left body sites to determine significant voltage value asymmetry between like right-left pairs of sites. The discrete bilateral anatomical dermal sites utilized for potential measurement yield measurably high D.C. bioelectric potentials and each like right-left side pair of sites is connected by deep natural inner body circuitry to a specific inner organ or biological system. If the inner organ or system is functioning in a healthy normal manner the D.C. bioelectric potentials at the electrically connected like bilateral sites approximate each other. If the inner organ or system is functioning in a diseased or abnormal manner the D.C. bioelectric potentials at the sites display a relatively high bilateral voltage variance.

8 Claims, 8 Drawing Figures

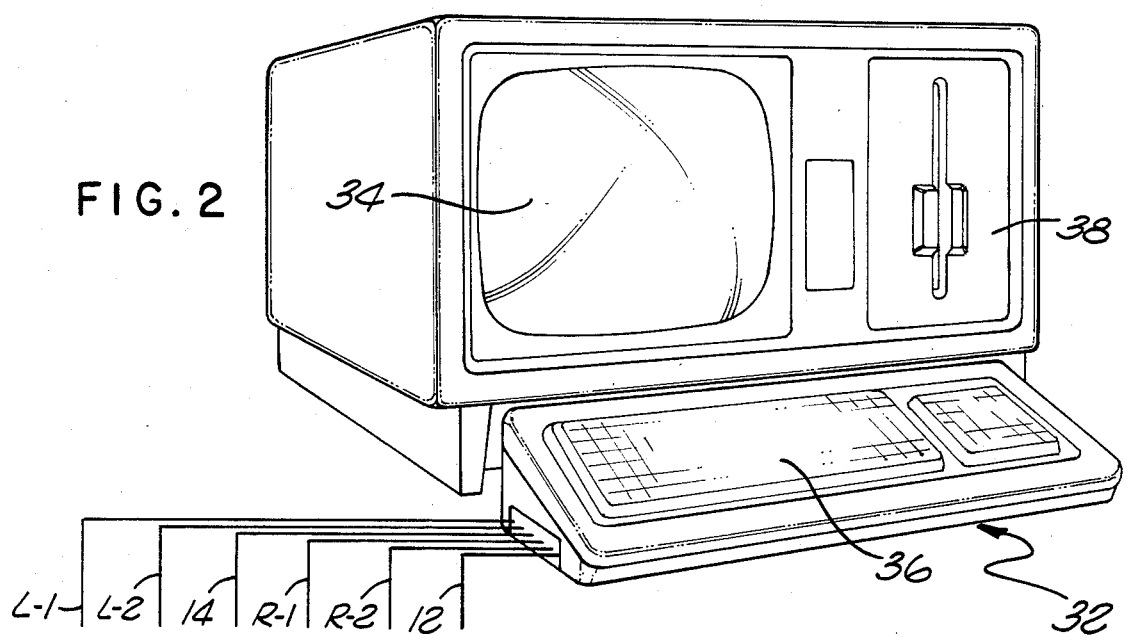
FIG. 2
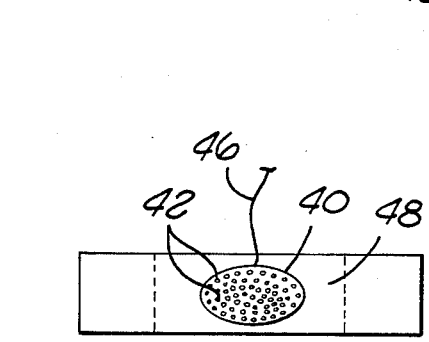
FIG. 3
FIG. 4
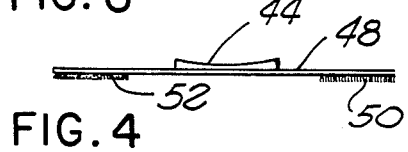
FIG. 5
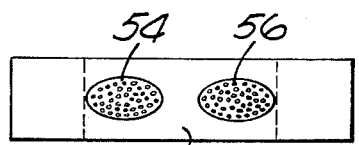
FIG. 6
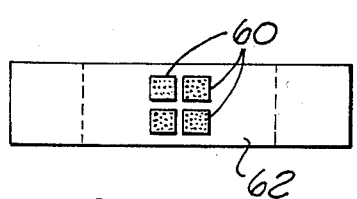
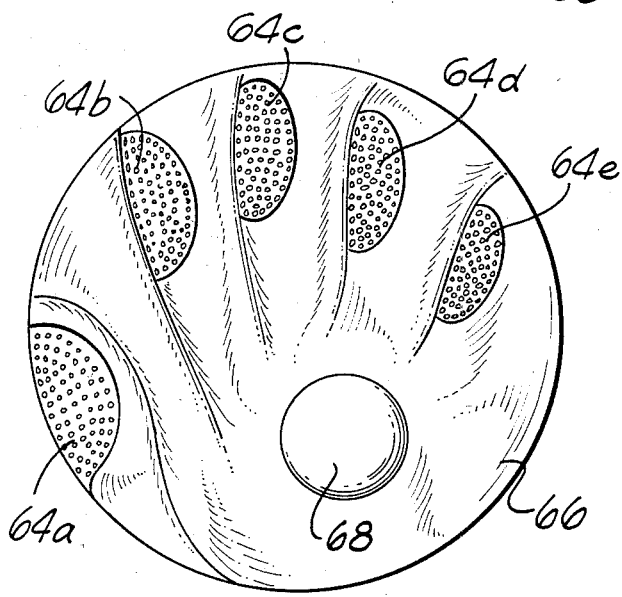
FIG. 7
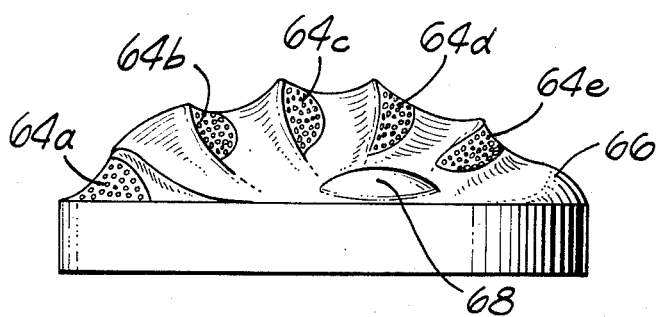
FIG. 8

METHOD AND APPARATUS FOR DETECTING BODY ILLNESS, DYSFUNCTION, DISEASE AND/OR PATHOLOGY

BACKGROUND OF THE INVENTION

The majority of illnesses that plague humans and other vertebrates involve disease and pathology associated with various internal organs such as the heart, lungs, kidneys, bladder, etc. Most often, an individual does not recognize the symptoms, if any, related to a disease process occurring in an internal organ and the problem goes untreated until gross symptoms appear at the physical level. Even if symptoms do appear, they all too frequently are not state specific, and therefore require a battery of highly specific and specialized tests to determine the precise location and nature of the disorder. Many of such tests are invasive of the body and create patient anxiety and cause physical discomfort or pain.

This invention relates to a method and apparatus for non-invasively measuring bioelectric potentials at selected dermal (skin) points on the body of man to detect existing or impending illness, dysfunction, disease and/or pathology. Direct current potentials on the dermal surfaces of man and other vertebrates have long been described, measured and correlated with a variety of biological functions. Standing D.C. potential patterns over the human body were described by H. S. Burr and F. S. C. Northrup in their paper entitled "The Electrodynamic Theory of Life," *Quarterly Review of Biology*, 1955 10, 322-333. More recently the D.C. potential fields have been mapped with some precision and the pattern has been found to be roughly parallel to the gross anatomical arrangement of the central nervous system. R. O. Becker concluded that two bioelectric data transmission and control systems coexist in man and most other present-day vertebrates, i.e., one a sophisticated, action potential, digital-type system, and the other, a more basic primitive analog-type system, "The Basic Biological Data Transmission and Control System Influenced by Electrical Forces," *Annals New York Academy of Sciences*, 1974, 236-241. Becker further observed D.C. voltage sources along the course of the peripheral data channels of the analog-type system. Such sites show lower resistence and higher voltage values which change significantly in response to irregularity or pathology in the body organs related to specific sites through the autonomic nervous system. Simply stated, the presence of some type of inrregularity or pathology in an organ or organ system related to a specific site produces a significant alteration of the D.C. potential at the dermal surface of such site.

This invention is related to the invention disclosed and claimed in our co-pending application Ser. No. 06/453,744 filed on Dec. 27, 1982 and entitled "Method and Apparatus for Detecting Ovulation."

SUMMARY OF THE INVENTION

The present invention relates to a method and apparatus that non-invasively measures and analyzes bilateral D.C. bioelectric potential functions associated with organized electrical field patterns about discrete anatomical sites on the dermal surface (skin) of human subjects for the express purpose of generating data for use by medical practitioners in diagnosing existing or impending illness, dysfunction, disease and/or pathology. The apparatus, termed a digital neurometer, simultaneously measures D.C. potentials at 10 to 14 bilateral dermal sites (principally finger and toe sites) through microgrid voltage sensing electrodes and develops a maximum bilateral D.C. potential differential value for each sensing electrode site with respect to a ground potential sensed by a ground electrode applied to the right side of the body of the subject and by a ground potential sensed by a ground electrode applied to the left side of the body of the subject. The instrumentation of the invention compares the 10 to 14 differential voltage values of the right body side sites with the 10 to 14 differential voltage values of the left body side sites to determine significant voltage value asymmetry between like right-left pairs of sites.

The discrete bilateral anatomical sites on the dermal surface of human subjects yield measurably high D.C. biopotentials and each right-left side pair of such sites is connected by deep inner body circuitry to a specific inner organ including the heart, lungs, stomach, liver, bladder, gall bladder, kidneys, spleen, large and small intestines, etc. If the inner organ is functioning in a healthy normal manner, the measurable D.C. biopotentials at the electrically connected bilateral anatomical (right and left side) sites approximate each other, i.e., display a relatively low bilateral voltage variance (15 millivolt difference or less). If the inner organ is functioning in a diseased or abnormal manner, the measurable D.C. biopotentials at the electrically connected bilateral anatomical sites display a relatively high bilateral voltage variance (greater than 15 millivolt difference).

Measurement of D.C. biopotentials at the electrically active bilateral anatomical sites, in accordance with the present invention, is accomplished through the use of D.C. potential sensing, microgrid electrodes (described in detail hereinafter) forming voltage input means to the digital neurometer instrumentation. For most measurement purposes the microgrid electrodes are interfaced with bilateral dermal sites on the fingers and toes of the subject. Generally, the microgrid sensing electrodes contact the terminal phalanx of the fingers and toes of the subject. The bilateral microgrid electrodes and bilateral ground electrodes are connected to a high input impedance linear amplifier which converts the very low D.C. biopotentials sensed by the microgrid electrodes and ground electrodes into low impedance higher voltage signals. Multiplexer circuitry directs the ordered transmission of all of the voltage signals sensed by each multigrid electrode (25 or more per electrode) over the respective electrode lead wire. An analog-to-digital converter converts the higher voltage outputs of the amplifier into a binary code of sensed voltages ranging between 0-999 millivolts.

Binary encoded information respecting the biopotentials sensed by the finger, toe and ground electrodes is passed from the converter through a data bus to a universal synchronous/asynchronous receiver-transmitter which polls and receives the binary voltage data from all points being sensed by the microgrid electrodes and the ground electrodes and transmits such data to a micro-dataprocessor (computer). The dataprocessor looks at the voltage data and selects the maximum biopotential value with respect to ground biopotential from each microgrid sensing electrode for storage, bilateral comparison, manipulation and reporting purposes. The micro-dataprocessor selects the specific micro-electrode point of dermal contact for each bilateral sensing microgrid electrode which yields the highest D.C. biopotentials with respect to the sensed respective right or left ground D.C. biopotential, subtracts the appropriate measured ground potential from the high value biopotentials and develops a reportable differential digital voltage value for each finger and toe site which can be compared bilaterally, right body side to left body side, to obtain a bilateral voltage variance value for each right-left pairs of sites. The digital differential values and digital variance values of a subject can be used by medical practitioners to analyze the physical condition of the subject and confirm normality of the subject's principal body organs or diagnose existing or impending illness, dysfunction, disease and/or pathology of the subject.

It is accordingly an object of this invention to provide a bioelectrical, D.C. potential-measuring method to be applied to selected bilateral dermal sites of human subjects to obtain D.C. potential values related to normal-abnormal states of principal body organs for diagnostic use by medical practitioners.

It is another object of the invention to provide a noninvasive, D.C. potential-measuring method to be applied to 10–14 bilateral dermal sites (principally finger and toe sites) of human subjects to obtain D.C. potential differential values, between such sites and a respective bilateral ground site, and to develop bilateral voltage variance values related to normal states and abnormal illness, dysfunction, disease or pathology states of principal body organs and systems for diagnostic use by medical practitioners.

It is a further object of the invention to provide a non-invasive, radiation-free D.C. potential-measuring apparatus to be applied to 10–14 bilateral dermal sites (principally finger and toe sites) of human subjects via microgrid biopotential sensing electrodes and ground electrodes to obtain D.C. potential differential values, between such sites and a respective bilateral ground site, and to develop bilateral digital voltage variance values related to normal sites and abnormal illness, dysfunction, disease or pathology states of the principal body organs and systems for diagnostic use by medical practitioners.

It is yet another objective of the invention to provide, in such non-invasive apparatus, means for scanning the bilateral dermal sites in contact with such microgrid biopotential sensing electrodes to locate specific points of maximum D.C. potential with respect to ground, measuring the differential voltage value at such points (with respect to ground potential) and comparing the bilateral differential voltage values to obtain digital voltage variance values related to normal states and abnormal illness, dysfunction, disease or pathology states of the principal body organs and systems and means for reporting the differential voltage values and voltage variance values in digital display or print-out fashion for diagnostic use by medical practitioners.

BRIEF DESCRIPTION OF THE DRAWING

The foregoing and other objects, features and advantages of the invention will become apparent hereinafter from the following detailed description of the invention taken in conjunction with the accompanying drawing wherein:

FIG. 2 is a schematic diagram of a computer console and visual display screen comprising part of the digital neurometer system of FIG. 1;

FIG. 3 is a top view of one form of finger-wrap or toe-wrap microgrid electrode for measureing D.C. potential differential values at dermal sites on the fingers and toes of the human body;

FIG. 4 is a front view of the microgrid electrode of FIG. 3;

FIG. 5 is a top view of a second form of wrap type microgrid electrode for measuring D.C. potential differential values at dermal sites on fingers and toes;

FIG. 6 is a top view of a third form of wrap type microgrid electrode for measuring D.C. potential differential values at dermal sites on fingers and toes;

FIG. 7 is a top view of a unitary multi-electrode unit for measuring D.C. potential differential values at dermal sites on the thumb and fingers of a human hand; and FIG. 8 is a front view of the multi-electrode unit of FIG. 7.

DETAILED DESCRIPTION OF THE INVENTION

Figure 1:
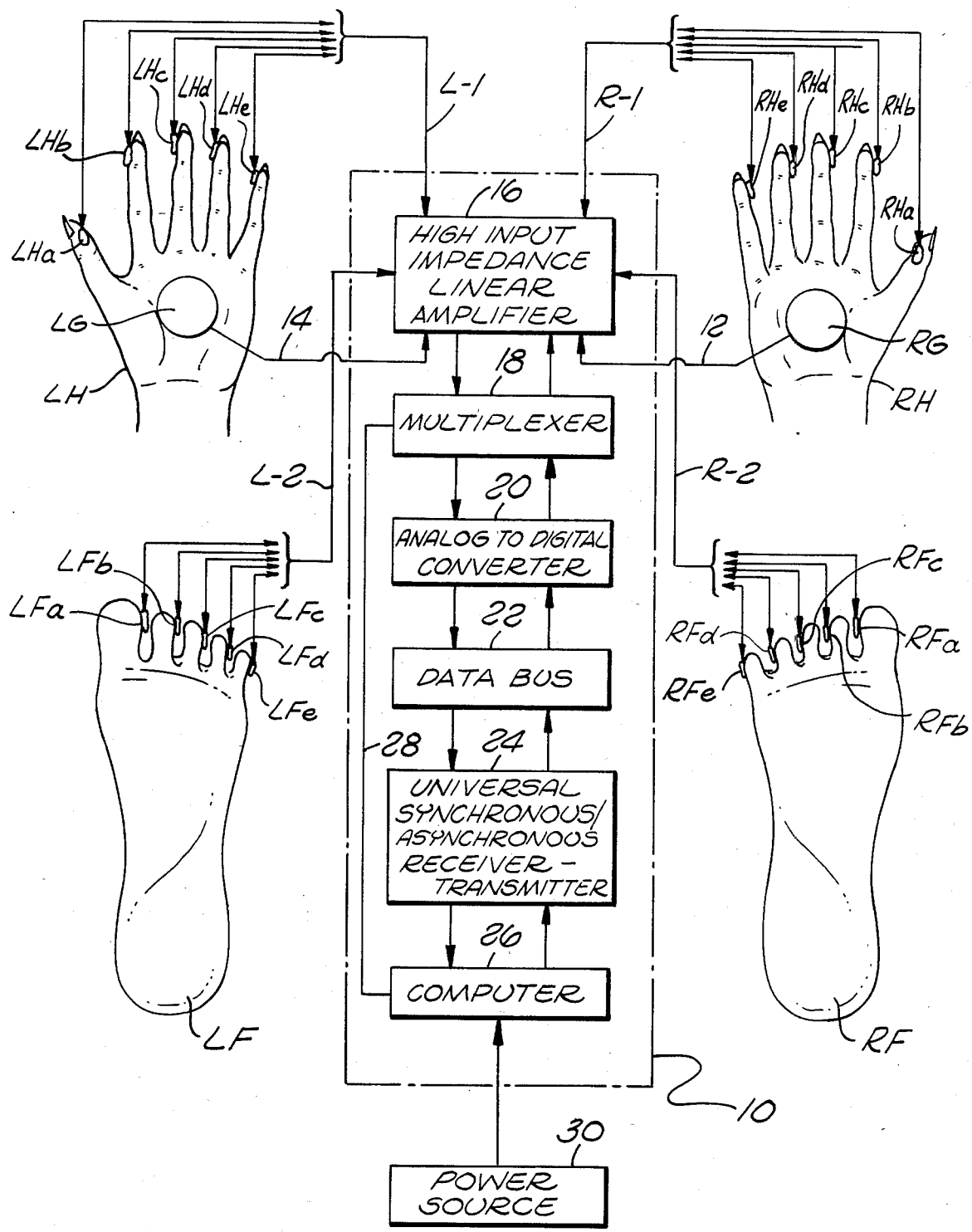
FIG. 1 is a basic block circuit diagram of the digital neurometer of the present invention applied to ten pairs of bilateral, symmetric electro-active dermal sites of the human body.

Referring now to the drawings, a preferred embodiment of the invention is illustrated in FIG. 1 and includes a basic block circuit diagram of the digital neurometer instrument 10 electrically connected through multi-wire cables R-1, R-2, L-1 and L-2 to D.C. potential sensing electrodes in contact, respectively, with the fingers of the right hand RH, toes of the right foot RF, fingers of the left hand LH, and toes of the left foot LF of a human subject undergoing non-invasive measurement of a multiplicity of body bioelectrical potentials. A bilateral D.C. potential differential value for each sensing electrode site is developed by the neurometer instrument with respect to ground potentials, respectively, on the right and left side of the subject's body. As shown in FIG. 1, ground potential for the right body side is developed through ground electrode RG impressed at the palm of the right hand and ground potential for the left body side is developed through ground electrode LG impressed at the palm of the left hand which are connected, respectively, to the neurometer instrument 10 through ground leads 12 and 14.

The multi-wire cables R-1, R-2, L-1 and L-2 are, respectively, subdivided into distinct wire clusters connected to the D.C. potential sensing electrodes RHa–e, RFa–e, LHa–e and LFa–e which in and of themselves comprise sets of micro-electrodes formed of a multiplicity of highly-conductive, separated wires (gold, silver or copper) set in an insulating matrix material so as to present a microgrid of wire-end contact points with the finger or toe surface areas interfacing with such sensing electrodes. Various forms of microgrid sensing electrodes (as described hereinafter) may be used in connection with the digital neurometer instrument 10 of the present invention. Thus, through such sensing electrodes and the associated circuitry of the neurometer instrument dermal finger and toe sites on both sides of the body of a subject are monitored to locate the point within such sites which presents the highest D.C. potential value with respect to ground potential (on the same body side), measure the differential D.C. potential value between the highest value point and respective ground, and compare the differential values on one side of the subject's body with a like differential value monitored, located and measured with respect to ground on the other side of the subject's body.

Generally, the microgrid sensing electrodes contact the terminal phalanx of the fingers and toes of the subject and, through multi-wire cables R-1, R-2, L-1 and L-2, are connected to input terminals of a high input impedance linear amplifier section 16 of the digital neurometer instrument 10. The ground electrodes, through ground leads 12 and 14 are likewise connected to ground input terminals of the high input impedance linear amplifier section of the neurometer. In the amplifier section 16 the very low D.C. biopotentials sensed by the microgrid sensing electrodes are converted to low impedance higher voltage signals. A multiplexer section 18 provides instrument 10 with the system means for transmitting all of the voltage signals from each multigrid sensing electrode over its respective single electrode lead wire. An analog-to-digital converter 20 converts the higher voltage outputs of amplifier 16 into a binary code of sensed voltages ranging between 0–999 millivolts. Binary encoded information respecting the biopotentials sensed by the finger, toe and ground electrodes is passed from the converter 20 through a data bus 22 to a universal synchronous/asynchronous receiver-transmitter 24. The receiver-transmitter polls and receives binary voltage data from all points being sensed by the microgrid finger and toe sensing electrodes (each having multiple points of dermal contact) and ground electrodes (each having a broad area of dermal contact) in an ordered fashion and transmits such data to a micro-dataprocessor (computer) 26 which looks at the voltage data and selects the maximum biopotential value with respect to ground biopotential from each microgrid sensing electrode for storage, bilateral comparison, manipulation and reporting purposes. Thus, the micro-dataprocessor selects the specific right and left side finger and toe sites yielding the highest D.C. biopotential with respect to the sensed respective right or left ground D.C. biopotential, subtracts the appropriate measured ground potential from the high value finger and toe potentials and develops a reportable differential, digital D.C. potential value for each finger and toe site which can be compared bilaterally, right body side value to left body side value. Further, the computer 26 can query and control each microgrid dermal contact point of each sensing electrode through multiplexer select control lines 28.

The micro-dataprocessor 26 includes appropriate memory circuitry and interfaces with visual display means and printer circuitry whereby compared bilateral D.C. potential values may be reported in digital display fashion or printed out. Further, the micro-dataprocessor may include means to receive programs and data bank information for comparing inter- and intra-subject (patient) biopotential data and disease, illness, dysfunction and/or pathological patterns and may direct the visual display or currently monitored data in comparison with data bank information on normal values and diagnostic indication on a displayed anatomical configuration or graphic mapping of the subject. The digital neurometer instrument 10 is electrically energized by an appropriate power source 30. An important feature of the instrumentation apparatus of the invention is that the instrument and its electrodes are non-invasive of the subject's body and no electrical charge or stimulus is applied to the body by the device.

FIG. 2 is a schematic diagram of a typical computer console 32 and visual display screen 34 arrangement for the digital neurometer instrument of the invention showing multi-wire cables R-1, R-2, L-1 and L-2 for input connection of the right and left finger and toe microgrid electrodes and for input connection of right and left ground leads 12 and 14. The computer console 32, as shown in FIG. 2 also includes a data input and retrieval keyboard 36 and data storage disc sections 38.

FIGS. 3 and 4 illustrate one form of a finger-wrap or toe-wrap microgrid electrode for measuring D.C. potential values over dermal site areas on the fingers and toes of the human body. The microgrid electrode 40 comprises a multiplicity of highly-conductive, separate wires 42 (gold, silver or copper) set in an insulating matrix material such as epoxy resin. The dermal interfacing surface 44 of the electrode 40 may be slightly concave in shape and is highly polished so as to present a microgrid of wire-end contact points (25 or more) with the finger or toe surface interfacing with the electrode. The multi-wire finger or toe electrode 40 is connected to the digital neutrometer instrument 10 through lead 46 and the electrical biopotential at each wire end is scanned by the instrument circuitry until a point site on the subject's finger or toe is located which presents the highest D.C. potential value with respect to ground potential on the same side of the subject's body. Such circuitry, after locating the high value point site, measures the differential D.C. potential value between the site and ground and reports such differential value in visual digital display or print-out fashion and compares such value with a bilateral site value in the visual display or printout. The microgrid electrode, as shown in FIG. 3 is oval shaped (may have a maximum dimension of about 10 millimeters and a minimum dimension of about 6–8 millimeters) and is affixed to a wrap band 48 which may be made of an elastic or fabric material and has means at its ends for securing the band as a wrap around a finger or toe or in band-aid adhesive fashion to a dermal surface. A preferred wrap-fastening means, as shown in FIG. 4, comprises "VELCRO" hook and eye fabric connector surfaces 50 and 52, respectively. The microgrid electrode 40 may be constructed of flexible "Mylar" plastic material imprinted with an array of copper, gold or gold-plated copper micro-electrode dots. Whether the microgrid electrode 40 is formed of an array of wire end contact points or printed conductive dots, each wire-end point or conductive dot has a diameter of about 0.5 millimeter.

In FIG. 5 there is illustrated a second form of wrap type microgrid sensing electrode arrangement wherein two sensing electrodes 54 and 56 are carried by a wrap band 58. Through such an arrangement two distinct and separate dermal areas of a given phalanx section of a finger or toe may be monitored by microgrid sensing electrodes to select and measure points having highest D.C. potential.

A further form of wrap type microgrid sensing electrode is shown in FIG. 6 wherein a mosaic arrangement of micro-electrode dots are imprinted on inflexible circuit boards or chips 60 which are affixed to a wrap band 62 and together form a microgrid electrode for use with the method and apparatus of this invention. Each circuit board or chip 60 may measure about 5 millimeters on a side and present an array of 25 micro-dot electrodes.

In FIGS. 7 and 8 there is illustrated further means for positioning five finger electrodes 64 a–e on a contoured palm and finger positioning platen 66. The contoured platen 66 also carries and presents a palm ground electrode 68 which contacts a central area of the subject's palm surface when the subject's hand (with fingers) is appropriately impressed against the platen with each finger seated against its respective concaveshaped finger microgrid electrode 64. The contoured platen 66 may be molded or cast of plastic or other non-conducting material and may be fabricated with its electrodes in a number of hand sizes for both right and left hand use. In like fashion, molded foot platens (bearing contoured toe microgrid sensing electrodes) may be fabricated with a ground electrode positioned for surface contact with the middle area of the subject's foot arch.

Use of the method and apparatus of the present invention for non-invasively measuring bilateral bioelectrical potentials of human subjects for developing significant and reliable diagnostic data for discovering and predicting disease, illness, dysfunction and/or pathology, is further described in the following exemplary use of the invention with respect to a statistically significant group of healthy, at risk and diseased subjects.

EXAMPLE

Using digital neurometer instrumentation substantially as described and illustrated herein, D.C. biopotentials were measured at ten bilateral dermal sites on 95 subjects who had come to their physicians for routine examination. On the basis of their current medical histories and clinical diagnosis, based on physical examinations as well as on appropriate laboratory tests (x-ray, EKG, etc.), as given by their physicians, they were placed into three groups: (1) healthy (20 subjects); (2) healthy-at-risk (17 subjects); and (3) disease (58 subjects). Those subjects with subacute conditions were placed in the healthy-at-risk group. Those subjects with disease had one or more of the following conditions: (1) cardiovascular disease (ischemic heart disease, congestive heart failure, moderate to severe hypertension, etc.); (2) pulmonary disease (chronic obstructive lung disease, pulmonary edema, etc.); (3) liver disease (hepatitis, cirrhosis, cholelithiasis, etc.); (4) genitourinary disease (prostatic cancer, urinary tract infections, etc.); (5) metabolic/endocrine disease (diabetes, Graves' disease, etc.); (6) gastrointestinal disease (reflux esophagitis, peptic ulcers, diverticulitis, etc.). Subjects were excluded from the study if they were: unable to relax (this would cause unstable variability in their D.C. potentials); in a fasting state (this could mimic gastrointestinal distress); or had any visible and/or grossly audible signs of disease, e.g., edema, morbid obesity, jaundice, wheezing, petechiae, etc. The dermal site D.C. potential measurements for each subject were taken by a medical technician blind to the subjects' medical histories.

Electrical potentials were measured in the 1 $\mu$V–700 mV range with instrument circuitry which utilized automatic gain control and ranging. Non-invasive bilateral skin contact was made via an electrode adapted to scan sites on the fingers and toes of each subject. The ground electrode was a 101.6 mm $\times$ 19.05 mm diameter cylindrical element held by the subject in either the right or left hand depending upon whether the scanning electrode was measuring a point on the right or left side of the body respectively (clean skin surfaces were unprepared). The measurement of potential did not require any applied current to be passed into the subject (can alter the electrical field at the dermal point-sources of D.C. biopotential). A consistent electrode-skin interface was maintained to obtain reproducible values. This was achieved utilizing a pressure-constant probe. Note: The absolute potential at any given D.C. point-source is subject to a number of factors which can alter that value at any moment including physical distress, a change in mood, or state or alertness; therefore, multiple determinations were made at each point-pair to minimize the possibility of obtaining a false bilateral variance. Factors which could have caused generalized individual variation of dermal electrical properties, such as dermal moisture content, were not parameters since the bilateral D.C. potential comparisons were made between the right and left sides of the same subject and not between subjects.

Ten bilateral sources of D.C. biopotential were chosen for study on the basis of 3 criteria: (1) all 10 point-pairs could be located on all subjects; (2) there were minimum inter-individual anatomic variations regarding point location; (3) all 10 point-pairs shared similar electrical parameters, i.e., the absolute potential at any given point was always $>37$ mV. The 10 point-pairs corresponded to the following respective anatomic locations: (1) dorsal aspect, terminal phalanx of the second toe-proximal to nail bed (PTNB); (2) lateral aspect, terminal phalanx of the fourth toe-PTNB; (3) lateral aspect, terminal phalanx of the fifth toe-PTNB; (4) plantar aspect of the foot between second and third metatarsals; (5) dorsal-lateral aspect of the first toe-PTNB; (6) dorsal-medial aspect of the first toe-PTNB; (7) ventral aspect, terminal phalanx of the fifth finger-distal to the interphalangeal joint; (8) radial aspect, terminal phalanx of the first finger-PTNB; (9) radial aspect, terminal phalanx of the second finger-PTNB; (10) ulnar aspect, terminal phalanx of the fifth finger-PTNB.

Results

The differential between the highest and lowest D.C. millivolt biopotentials for each point-pair of dermal sites is called the bilateral variance. A mean bilateral variance was obtained for each point-pair for the subjects in each group. Group means were compared by the two-sample t-test. A maximum bilateral variance was obtained from among each subject's 10 point-pairs and the respective groups were then compared by the accepted statistical chi-square test. The results of the two-sample t-test and chi-square test are set forth in Table I and Table II, respectively.

TABLE I

TWO-SAMPLE t-TEST
Analysis of Mean Bilateral Variance

| Group Comparison | Degrees of Freedom | Probability of Error |
|---|---|---|
| Disease vs. Healthy | 76 | $P < 0.0005$ |
| Disease vs. Healthy-at-Risk | 73 | $P < 0.0005$ |
| Healthy vs. Healthy-at-Risk | 35 | $P < 0.5$ |

Note:
Each group showed a normal distribution. Standard deviation (S) and the mean ($\bar{x}$) for each group: Disease S = 6.37, $\bar{x}$ = 13.6; Healthy-at-Risk S = 1.93, $\bar{x}$ = 4.69; and Healthy S = 2.17, $\bar{x}$ = 4.07.

TABLE II

CHI-SQUARE TEST
Maximum Bilateral Variance - Subject Distribution

| Maximum Bilateral Variance | Healthy Group | Health-at-Risk Group | Disease Group |
|---|---|---|---|
| $>15$ mV | 1 | 2 | 58 |
| $<15$ mV | 19 | 15 | 0 |

Note:
Chi-square = 79.9; 2 degrees of freedom ($P < 0.0005$).

Analysis of the data by the two-sample t-test (Table I) indicates that the difference betwen the mean bilateral variance of the healthy and healthy-at-risk groups is not significant ($P<0.5$), whereas the difference in the mean bilateral variance between the disease and healthy or healthy-at-risk groups is highly significant ($P<0.0005$). Each group is divided into 2 categories based on the number of the subjects whose maximum bilateral variance is $<15$ mV or $>15$ mV (Table II). The chi-square value obtained from the above categories is highly significant ($P<0.0005$), with the $<14$ mV–$>17$ mV range producing the largest chi-square value.

Discussion

The data reported via the digital neurometer instrumentation for the above 95 subjects indicates the diseased or ill subjects exhibited asymmetric dermal electrical fields at the tested sites which are discrete sources of D.C. biopotential. Of the 58 subjects who are placed in the disease group, all 58 showed a maximum bilateral variance of $>17$ mV at one or more of the 10 bilateral D.C. sources while all but 3 of the 37 subjects in the healthy or healthy-at-risk groups showed a maximum bilateral variance of $<14$ mV. The mean bilateral variance of the disease group was significantly different from the mean bilateral variance of either the healthy or healthy-at-risk groups, supporting the hypothesis that ill individuals exhibit asymmetric dermal D.C. bioelectric fields. These data suggest that the discrete dermal D.C. sources are sites of operational amplification for an electronic analog control system that acts as a biological regulator for healing mechanisms. The ability of medical practitioners to interpret the signals of the system has important implications since the phenomena of asymmetry found with disease holds the promise of being a non-invasive diagnostic evaluative tool.

From the foregoing example, it will be obvious that the present non-invasive method and apparatus for measuring D.C. bioelectrical potentials at selected dermal sites on human subjects provides means for obtaining analytical data susceptible to analysis by medical practitioners for discovering and/or predicting illness, dysfunction, disease and/or pathology.

While the invention has been described in connection with a particular structural embodiment of a digital neurometer and electrode means for locating and measuring highest D.C. biopotentials at specific dermal sites, many modifications of the neurometer apparatus and method of determining multiple bilateral biopotential variances will be apparent to those skilled in the art. Accordingly, such modifications are to be included within the spirit and scope of the invention as defined by the following claims.

We claim:

1. Apparatus for the non-invasive measurement and reporting of D.C. bioelectric potentials associated with organized electrical field patterns about discrete bilateral anatomical sites on the dermal surface of the body of a human subject to determine voltage value symmetry or asymmetry between like bilateral sites as an indication of body organ or biological system normality or abnormality comprising:

(a) a multiplicity of pairs of microgrid D.C. bioelectric potential sensing electrodes each including a multiplicity of separated wires adapted for multipoint bilateral contact with said discrete bilateral anatomical dermal sites for sensing a multiplicity of D.C. bioelectric potentials at each of said dermal sites;

(b) a pair of single wire ground electrodes adapted for bilateral D.C. bioelectric potential sensing contact with the body of said subject at dermal sites on the right and left body sides remote from the contact sites of said microgrid electrodes;

(c) means for receiving the multi-point D.C. bioelectric potentials sensed by said microgrid electrodes and the D.C. bioelectric potential sensed by said single wire ground electrodes and for converting said D.C. biopotentials to low impedance higher voltage signals, said D.C. bioelectric potential receiving and converting means including a high input impedance linear amplifier having input terminals in electrical communication with the multiplicity of wires of said microgrid electrodes and the single wire ground electrodes;

(d) means for converting said higher voltage signals into a binary code of sensed digital voltage values, said signal converting means including an anolog-to-digital converter having input terminals in electrical communication with said high input impedance linear amplifier;

(e) means for receiving coded binary digital voltage values from said analog-to-digital converter, polling said voltage values and placing said voltage values in ordered format, said voltage value receiving means including a universal synchronous/asynchronous receiver-transmitter having input terminals in electrical communication with said analog-to-digital converter;

(f) micro-dataprocessor means in electrical communication with said receiver-transmitter for receiving ordered voltage values from said receiver-transmitter, for selecting the highest voltage value sensed by each bilateral microgrid D.C. bioelectric potential sensing electrode in multi-point contact with the dermal surface at a discrete dermal site with respect to the voltage value sensed by the ground electrode on the same body side as each of said microgrid sensing electrodes, for developing a reportable differential, digital D.C. voltage value between said highest voltage value and said ground voltage value for each bilateral anatomical dermal site sensed by said bilateral microgrid sensing electrodes, and for developing a reportable bilateral digital voltage variance value between the differential values of each pair of like anatomical dermal sites; and (g) means for receiving said differential voltage values for each bilateral dermal site and said voltage variance values for each pair of like dermal sites from said micro-dataprocessor and reporting same in digital form as numerical values of D.C. bioelectric potential and numerical variance values of D.C. bioelectric potential related to normal and abnormal states of the principal body organs or biological systems.

2. Apparatus for the non-invasive measurement and reporting of D.C. bioelectric potentials on the dermal surface of the body of a human subject as defined in claim 1 wherein 10–14 pairs of said microgrid D.C. bioelectric potential sensing electrodes are provided to sense the multiplicity of D.C. bioelectric potentials associated with the organized electrical field patterns about discrete bilateral anatomical sited on the dermal surface of a human subject.

3. Apparatus for the non-invasive measurement and reporting a D.C. bioelectric potentials on the dermal surface of the body of a human subject as defined in claim 1 wherein 5 or more of the microgrid D.C. bioelectric potential sensing electrodes adapted for multipoint bilateral contact with dermal sites are mounted on solid platens contoured to receive the palm and fingers of the subject's hand or the arch and toes of the subject's foot.

4. Apparatus for the non-invasive measurement and reporting of D.C. bioelectric potentials on the dermal surface of the body of a human subject as defined in claim 3 wherein each of the solid platens contoured to receive the palm and fingers of the subject's hand or the arch and toes of the subject's foot carries one of the single wire ground electrodes for contact, respectively, with the palm of the subject's hand or arch of the subject's foot.

5. A method for non-invasively measuring and reporting D.C. bioelectric potentials associated with organized electrical field patterns about discrete bilateral anatomical sites on the dermal surface of the body of a human subject to determine voltage value symmetry or asymmetry between like bilateral sites as an indication of body organ or biological system normality or abnormality comprising:

(a) establishing electrical contact between discrete bilateral anatomical dermal sites on the body of a human subject and a multiplicity of multi-point bilateral microgrid D.C. bioelectric potential sensing electrodes including a multiplicity of separated wires for sensing a multiplicity of D.C. bioelectric potentials at each of said dermal sites;

(b) establishing electrical contact between the body of said subject and D.C. bioelectric potential sensing single wire ground electrodes at bilateral dermal sites on the right and left body sides remote from the contact sites of said microgrid sensing electrodes for sensing the D.C. bioelectric potentials at said remote sites;

(c) amplifying the multiplicity of D.C. bioelectric potentials sensed by said microgrid sensing electrodes and the D.C. bioelectric potentials sensed by said single wire ground electrodes through a high input impedance linear amplifier to produce low impedance higher voltage signals;

(d) converting said higher voltage signals into a binary code of sensed digital voltage values through an analog-to-digital converter;

(e) polling said coded sensed digital voltage values and placing said values in ordered format through a universal synchronous/asynchronous receiver-transmitter;

(f) processing said ordered digital voltage values through a micro-dataprocessor to select the highest voltage value sensed by each bilateral microgrid D.C. bioelectric potential sensing electrode with respect to the digital voltage value sensed by the ground electrode on the same body side as each of said microgrid sensing electrodes, developing a reportable differential, digital D.C. voltage value through said micro-dataprocessor between said highest voltage value and said ground voltage value for each anatomical dermal site sensed by said bilateral microgrid sensing electrodes, and developing a reportable bilateral digital voltage variance value through said micro-dataprocessor between the differential voltage values of each pair of like anatomical dermal sites; and (g) reporting said differential voltage values for each bilateral dermal site and said voltage variance values for each pair of like dermal sites in digital form as numerical values of D.C. bioelectric potential and numerical variance values of D.C. bioelectric potential related to normal or abnormal states of the principal body organs.

6. A method for non-invasively measuring and reporting D.C. bioelectric potentials on the dermal surface of the body of a human subject as defined in claim 5 wherein the electrical contact between dermal sites on the body of a human subject and the multiplicity of multipoint bilateral D.C. bioelectric potential sensing electrodes is established at 10-14 discrete bilateral anatomical dermal sites.

7. A method for non-invasively measuring and reporting D.C. bioelectric potentials on the dermal surface of the body of a human subject as defined in claim 6 wherein the 10-14 discrete bilateral anatomical dermal sites are on the fingers and toes of said subject.

8. A method for non-invasively measuring and reporting D.C. bioelectric potentials on the dermal surface of the body of a human subject as defined in claim 5 wherein the electrical contact between the body of a human subject and the D.C. bioelectric potential sensing ground electrodes is established on the palm of the hands of said subject.

* * * * *